US008609043B2

(12) United States Patent
Mattern

(10) Patent No.: US 8,609,043 B2
(45) Date of Patent: Dec. 17, 2013

(54) USE OF A CONTAINER OF AN INORGANIC ADDITIVE CONTAINING PLASTIC MATERIAL

(75) Inventor: Claudia Mattern, Stans (CH)

(73) Assignee: M & P Patent Aktiengesellschaft, Vaduz (LI)

( * ) Notice: Subject to any disclaimer, the term of this patent is extended or adjusted under 35 U.S.C. 154(b) by 0 days.

(21) Appl. No.: 13/567,878

(22) Filed: Aug. 6, 2012

(65) Prior Publication Data
US 2012/0297730 A1    Nov. 29, 2012

Related U.S. Application Data

(63) Continuation of application No. 13/194,663, filed on Jul. 29, 2001, now abandoned, which is a continuation of application No. 13/152,882, filed on Jun. 3, 2011, now abandoned, which is a continuation of application No. 11/027,699, filed on Dec. 28, 2004, now abandoned.

(51) Int. Cl.
*B01L 3/00*    (2006.01)

(52) U.S. Cl.
USPC ........... 422/547; 422/400; 422/401; 422/408; 422/500; 422/549; 422/550; 422/554; 422/556; 422/557; 422/558; 422/559; 422/560; 422/561; 422/939; 422/940; 436/164; 436/165; 436/169; 436/170; 436/817; 436/815; 435/13; 435/283.1; 435/287.1; 435/287.8; 435/287.9; 435/288.7; 106/499; 128/203.18; 128/203.21; 128/203.22; 156/69; 206/219; 206/438; 206/828; 424/1.13; 424/400; 424/404; 424/434; 424/435; 424/45; 514/1; 514/170; 514/97; 514/9.8; 514/10.2

(58) Field of Classification Search
USPC ......... 422/500, 547, 400, 401, 408, 549, 550, 422/554, 556, 557, 558, 559, 560, 561, 939, 422/940; 206/438, 219, 828; 436/164, 165, 436/169, 170, 815, 817; 435/13, 283.1, 435/287.1, 287.7, 287.8, 287.9, 288.7; 106/499; 128/203.18, 203.21, 203.22; 156/69; 424/1.13, 400, 404, 434, 435, 424/45; 514/1, 12, 14, 170, 9.7, 9.8, 10.2
See application file for complete search history.

(56) References Cited

U.S. PATENT DOCUMENTS

| 3,923,190 | A | 12/1975 | Roth |
| 4,051,265 | A | 9/1977 | Kirshenbaum et al. |
| 4,071,623 | A | 1/1978 | Van der Vies |
| 4,083,973 | A | 4/1978 | Van der Vies |
| 4,123,417 | A | 10/1978 | Finberg |
| RE29,892 | E | 1/1979 | Bayne |
| 4,546,882 | A | 10/1985 | Hsu et al. |
| 4,752,425 | A | 6/1988 | Martin et al. |
| 4,786,678 | A | 11/1988 | Dobreski et al. |
| 4,812,448 | A | 3/1989 | Knepper |
| 4,826,852 | A | 5/1989 | Haffner et al. |
| 5,049,387 | A | 9/1991 | Amkraut |
| 5,397,771 | A | 3/1995 | Bechgaard et al. |
| 5,455,286 | A | 10/1995 | Amidon et al. |
| 5,500,261 | A | 3/1996 | Takei et al. |
| 5,624,960 | A | 4/1997 | Wenzel et al. |
| 5,645,856 | A | 7/1997 | Lacy et al. |
| 5,756,071 | A | 5/1998 | Mattern |
| 5,877,216 | A | 3/1999 | Place et al. |
| 5,891,920 | A | 4/1999 | Hirano et al. |
| 5,948,492 | A | 9/1999 | Cargile |
| 6,187,323 | B1 | 2/2001 | Aiache et al. |
| 6,231,662 | B1* | 5/2001 | Atkinson ................ 106/499 |
| 6,248,363 | B1 | 6/2001 | Patel et al. |
| 6,310,089 | B1 | 10/2001 | Watts et al. |
| 6,319,905 | B1 | 11/2001 | Mandel et al. |
| 6,432,440 | B1 | 8/2002 | Watts et al. |
| 6,669,879 | B1 | 12/2003 | Spengler et al. |
| 6,800,363 | B2 | 10/2004 | Su et al. |
| 6,815,506 | B2 | 11/2004 | Takashima et al. |
| 2001/0055569 | A1 | 12/2001 | Davis et al. |
| 2002/0032171 | A1 | 3/2002 | Chen et al. |
| 2002/0114933 | A1* | 8/2002 | Gould ..................... 428/212 |
| 2002/0136752 | A1 | 9/2002 | Whittle et al. |
| 2002/0198136 | A1 | 12/2002 | Mak et al. |
| 2004/0005275 | A1 | 1/2004 | Gizurarson et al. |
| 2005/0100564 | A1 | 5/2005 | Mattern |
| 2006/0140820 | A1 | 6/2006 | Mattern |
| 2007/0149454 | A1 | 6/2007 | Mattern |
| 2009/0227550 | A1 | 9/2009 | Mattern |

(Continued)

FOREIGN PATENT DOCUMENTS

| DE | 943792 | 6/1956 |
| DE | 1569286 | 10/1976 |

(Continued)

OTHER PUBLICATIONS

Ko et al "Emulsion formulations of testosterone for nasal administration" J. Microencapsulation, 1998, vol. 15, No. 2, pp. 197-205.*
Office Action issued on Jan. 13, 2012 by the Examiner in U.S. Appl. No. 12/796,165 (US 2010/0311707).
Office Action issued on Nov. 16, 2009 by the Examiner in U.S. Appl. No. 11/560,187 (US 2007/0149454).
Office Action issued on Mar. 18, 2009 by the Examiner in U.S. Appl. No. 11/560,187 (US 2007/0149454).
Office Action issued on Oct. 29, 2008 by the Examiner in U.S. Appl. No. 11/560,187 (US 2007/0149454).
Office Action issued on Aug. 20, 2008 by the Examiner in U.S. Appl. No. 11/560,187 (US 2007/0149454).
Office Action issued on Feb. 5, 2008 by the Examiner in U.S. Appl. No. 11/560,187 (US 2007/0149454).
Office Action issued on Sep. 14, 2007 by the Examiner in U.S. Appl. No. 11/560,187 (US 2007/0149454).

(Continued)

*Primary Examiner* — Dennis M White
(74) *Attorney, Agent, or Firm* — Foley & Lardner LLP

(57) ABSTRACT

The present invention relates to the use of a container, made of an inorganic additive containing plastic material, for reducing physical/chemical interaction between the container and an oil, fat and/or wax containing formulation contained therein.

22 Claims, No Drawings

(56) References Cited

U.S. PATENT DOCUMENTS

| | | | |
|---|---|---|---|
| 2010/0311707 | A1 | 12/2010 | Mattern |
| 2011/0237562 | A1 | 9/2011 | Mattern |
| 2012/0005987 | A1 | 1/2012 | Mattern |
| 2012/0009249 | A1 | 1/2012 | Mattern |
| 2012/0009250 | A1 | 1/2012 | Mattern |
| 2012/0058176 | A1 | 3/2012 | Mattern |
| 2012/0083480 | A1 | 4/2012 | Mattern |
| 2012/0277202 | A1 | 11/2012 | Mattern |
| 2012/0297730 | A1 | 11/2012 | Mattern |

FOREIGN PATENT DOCUMENTS

| | | |
|---|---|---|
| EP | 0 084 922 A2 | 8/1983 |
| EP | 0 160 501 | 11/1985 |
| GB | 761618 | 11/1956 |
| JP | 50-144579 | 11/1975 |
| JP | 54-072192 | 6/1979 |
| JP | 01016716 | 1/1989 |
| KR | 20-0282242 | 7/2002 |
| WO | WO 00/59512 | 10/2000 |
| WO | WO 02/051452 | 7/2002 |

OTHER PUBLICATIONS

Office Action issued on Jul. 8, 2010 by the Examiner in U.S. Appl. No. 10/772,964 (US 2005/0100564).
Office Action issued on Sep. 29, 2009 by the Examiner in U.S. Appl. No. 10/772,964 (US 2005/0100564).
Office Action issued on Jan. 15, 2009 by the Examiner in U.S. Appl. No. 10/772,964 (US 2005/0100564).
Office Action issued on May 5, 2008 by the Examiner in U.S. Appl. No. 10/772,964 (US 2005/0100564).
Office Action issued on Mar. 17, 2008 by the Examiner in U.S. Appl. No. 10/772,964 (US 2005/0100564).
Office Action issued on Apr. 4, 2007 by the Examiner in U.S. Appl. No. 10/772,964 (US 2005/0100564).
Office Action issued on Jul. 3, 2012 by the Examiner in U.S. Appl. No. 13/316,494 (US 2012/0083480).
Office Action issued on Nov. 5, 2012 by the Examiner in U.S. Appl. No. 13/194,928 (US 2012/0009250).
Office Action issued on Feb. 15, 2012 by the Examiner in U.S. Appl. No. 13/194,928 (US 2012/0009250).
Office Action issued on Nov. 9, 2011 by the Examiner in U.S. Appl. No. 13/194,928 (US 2012/0009250).
Office Action issued on Jul. 3, 2012 by the Examiner in U.S. Appl. No. 13/194,853 (US 2012/0058176).
Office Action issued on Aug. 14, 2012 by the Examiner in U.S. Appl. No. 13/194,853 (US 2012/0058176).
Office Action issued on Apr. 11, 2013 by the Examiner in U.S. Appl. No. 13/194,926 (US 2012/0009249).
Office Action issued on Sep. 19, 2012 by the Examiner in U.S. Appl. No. 13/194,926 (US 2012/0009249).
Office Action issued on May 30, 2012 by the Examiner in U.S. Appl. No. 13/194,926 (US 2012/0009249).
Office Action issued on Apr. 25, 2008 by the Examiner in U.S. Appl. No. 11/027,699 (US 2006/014820).
Office Action issued on Nov. 3, 2008 by the Examiner in U.S. Appl. No. 11/027,699 (US 2006/014820).
Office Action issued on Jan. 13, 2009 by the Examiner in U.S. Appl. No. 11/027,699 (US 2006/014820).
Office Action issued on Jul. 7, 2009 by the Examiner in U.S. Appl. No. 11/027,699 (US 2006/014820).
Office Action issued on Feb. 3, 2010 by the Examiner in U.S. Appl. No. 11/027,699 (US 2006/014820).
Office Action issued on May 6, 2010 by the Examiner in U.S. Appl. No. 11/027,699 (US 2006/014820).
Office Action issue on Jul. 14, 2011 by the Examiner in U.S. Appl. No. 13/152,882 (US 2011/0237562).
Office Action issued on Feb. 6, 2012 by the Examiner in U.S. Appl. No. 13/194,663 (US 2012/0005987).
International Search Report issued on Dec. 21, 2007 in application No. PCT/EP2007/008409.
Mattern et al., "Testosterone supplementation for hypogonadal men by the nasal route," The Aging Male, vol. 11, No. 4, pp. 171-178, Dec. 2008.
Banks et al., "Delivery of testosterone to the brain by intranasal administration: Comparison to intravenous testosterone," Journal of Drug Targeting, vol. 17, No. 2, pp. 1-7, Dec. 16, 2008.
Ko et al., "Emulsion formulations of testosterone for nasal administrations," J. Microencapsulation, vol. 15, No. 2, pp. 197-205, 1998.
Office Action issued on Jan. 6, 2011 by the Examiner in U.S. Appl. No. 12/418,917 (US 2009/0227550).
Office Action issued on Mar. 8, 2011 by the Examiner in U.S. Appl. No. 12/418,917 (US 2009/0227550).
Buddenberg, et al. *Behavioral actions of intranasal application of dopamine: effects on forced swimming, elevated plus-maze and open field parameters*, (Neuropsychobiology. 2008;57(1-2):70-9).
De Souza Silva, et al. *Increased Neostriatal Dopamine Activity After Intraperitoneal or Intrana.sal Administration of L-DOPA: On the Role of Benserazide Pretreatment*. (Synapse. 1997 27:294-302.
De Souza Silva, et al. *Intranasal administration of the dopaminergic agonists L-DOPA, amphetamine, and cocaine increases dopamine activity in the neostriatum: a microdialysis study in the rat*, (I Neurochem. Jan. 1997;68(1):233-9).
De Souza Silva, et al. *Intranasal Dopamine Application Increases Dopatninergic Activity in the Neostriatum and Nucleus Accumbens and Enhances Motor Activity in the Open Field*. (Synapse. Mar. 2008;62(3):176-84).
Tavares, et al. *Effects of intra-nasally administered testosterone on sexual proceptive behavior in female capuchin monkeys (Cebus apella)*. (Behav Brain Res. Apr. 16, 2007;179(1):33-42).
Topic, et al. *Prolonged effects of intra-nasally administered testosterone on sexual proceptive behavior in female capuchin monkeys (Cebus apella)*. (Behav Brain Res. Apr. 16, 2007;179(1):60-68).

\* cited by examiner

USE OF A CONTAINER OF AN INORGANIC ADDITIVE CONTAINING PLASTIC MATERIAL

CROSS-REFERENCE TO RELATED APPLICATIONS

This application is a continuation of U.S. patent application Ser. No. 13/194,663, filed Jul. 29, 2011, pending, which is a continuation of U.S. patent application Ser. No. 13/152,882, filed Jun. 3, 2011, pending, which is a continuation of U.S. patent application Ser. No. 11/027,699, filed Dec. 28, 2004, abandoned. The contents of each of the foregoing applications are incorporated herein by reference in their entirety.

FIELD OF THE INVENTION

The present invention relates to the use of a container of an inorganic additive containing plastic material.

DESCRIPTION OF THE RELATED ART

Plastic containers are readily used for pharmaceutical preparations. However it is known that, due to their character, there are some limitations. Thus to suppress the reactivity of containers from polyethylene or polypropylene and their copolymers/blends towards certain chemicals several methods are used: plasticizers are avoided which would increase the motility of the chain molecules, polymers of higher density or polyolefin blends (e.g. polypropylene/polyacrylate) are used, the wall thickness is increased or the containers are wrapped (e.g. aluminium foil) or sealed (e.g. fluorination, silicone).

U.S. Pat. No. 4,123,417 (Finberg, 1978) claims that the toughness of LDPE can be increased by a blend comprising low density polyethylene containing an amorphous ethylene-propylene copolymer having a certain amount of crystallinity and a specified ethylene content.

U.S. Pat. No. 4,546,882 (Hsu et al., 1985) claims a multiple layer package for oil-containing products comprising an oil barrier layer from nylon or ethylene vinyl alcohol.

U.S. Pat. No. 5,500,261 (Takei et al., 1996) claims an oil resistant container comprising a blended resin composition having specified glass-transition temperatures.

U.S. Pat. No. 6,800,363 (Su et al., 2004) claims a film that does not distort in the presence of food oils using a polyolefin multilayer film having a skin layer from oil-absorbing porous particles (calcium carbonate, silicone dioxide, amorphous silica, sodium aluminosilicate, activated charcoal) and a metallized layer.

U.S. Pat. No. 6,815,506 (Takashima et al., 2004) claims an oil-resistant thermoplastic elastomer composition comprising a propylene resin, an unsaturated group-containing acrylic rubber and an inorganic filler for rubber compositions, preferred silica.

Also other additives are usual to improve the properties of plastics. Of high importance are pigments and ultraviolet stabilizers (organic and inorganic pigments, dyes, benzophenone, hindered amines etc.). These cover a broad spectrum of requirements, such as heat stability, fastness to light and weathering, where titanium dioxide ($TiO_2$) is most common in pharmaceuticals. $TiO_2$ is an inert substance known for its broad spectrum of UV-absorption and non-migration (movement into the drug formulation).

SUMMARY OF THE INVENTION

It is an object of the invention to provide an alternative use of containers made of an additive containing plastic material, which containers contain an oil, fat and/or wax containing formulation.

This object is achieved by an use of a container, made of an additive containing plastic material, for reducing physical/chemical interaction between the container and an oil, fat and/or wax containing formulation contained therein.

Preferably, the physical/chemical interaction is an adsorption of the formulation to the plastic material.

More preferably, the inorganic additive is at least a pigment.

Most preferably, the at least one pigment is titanium dioxide ($TiO_2$), surface-treated titanium dioxide, or a mixture thereof.

In one embodiment, the additive is present in the plastic material in an amount between 0.1 and 10% by weight, more preferably between 0.1 and 5% by weight, and most preferably about 2% by weight, based on the weight of the plastic material.

The plastic material may comprises polyolefin.

Preferably, the polyolefin is selected from the group of polyethylene, polypropylene, copolymers of ethylene and propylene, or a mixture thereof.

More preferably, the plastic material comprises low density polyethylene (LDPE).

The plastic material may be suitable for extrusion blow molding.

Preferably, the formulation comprises at least one steroid hormone dissolved or suspended in oil, fat and/or wax.

More preferred, the steroid hormone is a sexual hormone drug, preferably testosterone, and the formulation further comprises at least one lipophilic or partially lipophilic carrier; and a compound or a mixture of compounds having surface tension decreasing activity, in an amount effective for in situ generation of an emulsion upon contact of the formulation with water.

Finally, the formulation is preferably for nasal application, preferably to a mammalian.

A preferred low density polyethylene is for example Lupolen® 1840 H. Further, a preferred formulation may be the one which is disclosed in EP 03025769.5.

Surprisingly, it was found that a container of an inorganic additive containing plastic material may be advantageously utilized for keeping oil, fat and/wax containing formulations, for example oily formulations of steroid hormones, in that the use of such a container will reduce physical-chemical interactions of the container and the formulation, especially the adsorption of the formulation to the plastic material.

Surprisingly, the inventor has found that $TiO_2$ can also be used for a purpose for which it was not intended to be used so far: By adding it to plastic packaging material the physical-chemical interaction of certain oily formulations with the container, restricting its use, can be prevented.

The approaches actually made dealing with oil—plastic interaction did not use inorganic additive auxiliary agents nor a possibility was described for protecting a corresponding steroid hormone containing formulation from adsorption to plastic.

DETAILED DESCRIPTION OF THE INVENTION

In nasal application forms the suitability of the device for administration is of major importance. This applies to improving patient's compliance by convenient administration. But this also applies to pharmaceutical necessities such as the uniformity of emitted dose and the compatibility of the formulation with the primary packaging material. In pharmaceutical applications it is essential to use inert material for primary packaging; the galenical formulation, the active ingredient and the excipients, should not adversely be influenced by any interaction.

In principle there are two materials and two types for packaging of nasal formulations: glass vs. plastic and multiple-dose vs. unit-dose containers. The main advantages of plastic materials are their flexibility allowing for a wide range of designs, low weight, shatter resistance, and easy handling. Especially suitable for nasal application are unit-dose containers from plastic because of their small size, because no pump mechanism is necessary nor the addition of preservatives to the product formulation.

As starting material for such plastic containers polyethylene or polypropylene and their copolymers are used. Possible drawbacks in respect of their use are the oxygen permeability, poor UV resistance and, due to the nonpolar character, degree of crystallinity and molar mass, the poor resistance to some chemicals.

Thus polyethylene and polypropylene are not generally resistant to aliphatic and aromatic hydrocarbons and their halogen derivatives as well as to low-volatility substances such as fats, oils and waxes. Incompatibilities which can be seen are adsorption of the chemicals to the plastic, diffusion and swelling by the chemicals, or even dissolution in the chemicals.

On the other hand hydrocarbon derivatives such as steroid hormones are readily formulated using oil as carrier to increase their solubility and time of action. To avoid stability problems caused by the primary packaging these oily formulations—mostly injectables—usually are filled into glass devices. This kind of packaging however is not suitable for all application forms, e.g. not for oily formulations for nasal application. In concern of multi-dose devices the reason is that, although the bottle might be from glass, there are always parts of the device, such as the pump, which are from plastic material. In concern of unit-dose devices the reason is that these, at least in the case of viscous formulations which have to be squeezed, cannot be made from glass but moulded from plastics, mostly by the blow-fill-seal technology.

As an example for the aforementioned considerations in table 1 are shown the results of tests investigating the stability of formulations containing the steroid hormone testosterone in containers of different material.

TABLE 1

Stability of formulations containing testosterone in containers of different material

| Primary packaging material | Formulation | Remaining drug after storage (%) |
|---|---|---|
| LDPE | Oil-based | ≈30% |
| PP | Oil-based | ≈50% |
| Glass | Oil-based | ≈80% |
| Glass | Methanolic | 100% |
| LDPE + $TiO_2$ | Oil-based | 100% |

The term "remaining drug after storage" is the amount of testosterone remaining in the formulation after storage for 22 hours. The remaining drug was measured by HPLC technique.

It is obvious that there is a complex interaction of the drug with the oily formulation and of the oily formulation with the primary packaging material. For clinical-pharmaceutical reasons however the oil-based formulation and a unit-dose device for packaging was preferred. Thus some effort was made by the applicant using complicated procedures to solve this problem. Surprisingly however after adding titanium dioxide to the plastic material by this simple step it was possible to increase the shelf-life of the pharmaceutical formulation.

The features disclosed in the foregoing description and in the claims may, both separately and in any combination thereof, be material for realizing the invention in diverse forms thereof.

The invention claimed is:

1. A method for reducing physical or chemical interactions between a nasal testosterone formulation and a plastic container comprising:
   providing the nasal testosterone formulation in the container, wherein the container is made of a plastic material that comprises an inorganic additive;
   wherein the nasal testosterone formulation comprises (i) testosterone, (ii) a lipophilic or partially lipophilic carrier, and (iii) a compound or a mixture of compounds having surface tension decreasing activity.

2. The method according to claim 1 wherein the method reduces adsorption of the formulation to the plastic material.

3. The method according to claim 1, wherein the inorganic additive comprises a pigment.

4. The method according to claim 3, wherein the pigment is selected from the group consisting of titanium dioxide ($TiO_2$), surface-treated titanium dioxide, and mixtures thereof.

5. The method according to claim 1, wherein the inorganic additive is present in the plastic material in an amount between about 0.1 and about 10% by weight based on the weight of the plastic material.

6. The method according to claim 1, wherein the plastic material comprises polyolefin.

7. The method according to claim 6, wherein the polyolefin is selected from the group consisting of polyethylene, polypropylene, copolymers of ethylene and propylene, and mixtures thereof.

8. The method according to claim 7, wherein the plastic material comprises low density polyethylene (LDPE).

9. The method according to claim 1, wherein the plastic material is suitable for extrusion blow molding.

10. The method according to claim 1, wherein the inorganic additive is present in the plastic material in an amount of between about 0.1% to about 5% by weight based on the weight of the plastic material.

11. The method according to claim 1, wherein the inorganic additive is present in the plastic material in an amount of about 2% by weight based on the weight of the plastic material.

12. The method of claim 1, wherein the method extends the shelf life and stability of the nasal testosterone gel formulation for a period of time longer than that of a method wherein the formulation is provided in a plastic container that does not comprise the inorganic additive.

13. A method for reducing physical or chemical interactions between a nasal testosterone formulation and a plastic container comprising:
   providing the nasal testosterone formulation in the container, wherein the container is made of a plastic material that comprises polyolefin and titanium dioxide, wherein the titanium dioxide is present in the plastic material in an amount between about 0.1 and about 10% by weight, based on the weight of the plastic material;

wherein the nasal testosterone formulation comprises (i) testosterone dissolved or suspended in a lipophilic or partially lipophilic carrier, and (ii) a compound or a mixture of compounds having surface tension decreasing activity.

14. The method according to claim 13, wherein the polyolefin is selected from the group consisting of polyethylene, polypropylene, copolymers of ethylene and propylene, and mixtures thereof.

15. The method according to claim 13, wherein the plastic material comprises low density polyethylene (LDPE).

16. The method according to claim 13, wherein the plastic material is suitable for extrusion blow molding.

17. The method according to claim 13, wherein the titanium dioxide is surface-treated titanium dioxide.

18. The method according to claim 13, wherein the titanium dioxide comprises titanium dioxide mixed with surface-treated titanium dioxide.

19. The method according to claim 13, wherein the titanium dioxide is present in the plastic material in an amount of between about 0.1% to about 5% by weight based on the weight of the plastic material.

20. The method according to claim 13, wherein the titanium dioxide is present in the plastic material in an amount of about 2% by weight based on the weight of the plastic material.

21. The method according to claim 13, wherein about 100% of the testosterone in the nasal testosterone formulation remains after 22 hours of storage in the container, as determined by high performance liquid chromatography (HPLC) technique.

22. A method for reducing adsorption of a nasal testosterone formulation onto a plastic container, comprising:
    storing the nasal testosterone formulation in the plastic container
    wherein the plastic container comprises a plastic material comprising polyolefin and titanium dioxide, wherein the titanium dioxide is present in an amount of between about 0.1 and about 10% by weight, based on the weight of the plastic material;
    wherein the nasal testosterone formulation comprises (i) testosterone; (ii) a lipophilic or partially lipophilic carrier, and (ii) a surfactant having surface tension decreasing activity.

* * * * *